(12) United States Patent
Schall et al.

(10) Patent No.: US 9,192,423 B2
(45) Date of Patent: Nov. 24, 2015

(54) HIGH FREQUENCY SURGERY GENERATOR

(75) Inventors: Heiko Schall, Nuertingen (DE); Martin Fritz, Tuebingen (DE)

(73) Assignee: ERBE ELEKTROMEDIZIN GMBH, Tübingen (DE)

( * ) Notice: Subject to any disclaimer, the term of this patent is extended or adjusted under 35 U.S.C. 154(b) by 355 days.

(21) Appl. No.: 13/512,840

(22) PCT Filed: Nov. 3, 2010

(86) PCT No.: PCT/EP2010/066726
§ 371 (c)(1),
(2), (4) Date: May 30, 2012

(87) PCT Pub. No.: WO2011/067061
PCT Pub. Date: Jun. 9, 2011

(65) Prior Publication Data
US 2012/0245579 A1    Sep. 27, 2012

(30) Foreign Application Priority Data
Jan. 25, 2010  (DE) .......................... 10 2010 000 184

(51) Int. Cl.
*A61B 18/12* (2006.01)
*H03L 7/099* (2006.01)
*A61B 18/00* (2006.01)

(52) U.S. Cl.
CPC ............ *A61B 18/1206* (2013.01); *H03L 7/099* (2013.01); *A61B 2018/00851* (2013.01)

(58) Field of Classification Search
CPC ............... A61B 18/1206; A61B 18/12; A61B 2018/00601; A61B 2018/00607; A61B 2018/128

USPC .......................................... 606/32–34, 37–42
See application file for complete search history.

(56) References Cited

U.S. PATENT DOCUMENTS

| | | | | | |
|---|---|---|---|---|---|
| 3,699,967 | A | * | 10/1972 | Anderson ........................ | 606/37 |
| 4,318,409 | A | * | 3/1982 | Oosten ............................ | 606/37 |
| 4,658,820 | A | * | 4/1987 | Klicek ............................ | 606/37 |
| 5,334,183 | A | * | 8/1994 | Wuchinich ...................... | 606/46 |
| 5,647,869 | A | * | 7/1997 | Goble et al. .................... | 606/37 |
| 6,093,186 | A | | 7/2000 | Goble | |

(Continued)

FOREIGN PATENT DOCUMENTS

| | | |
|---|---|---|
| CN | 1245410 | 2/2000 |
| DE | 2250574 A1 | 4/1974 |

(Continued)

OTHER PUBLICATIONS

International Search Report for PCT/EP2010/066726, English translation attached to original, Both completed by the European Patent Office on Jul. 4, 2010, All together 5 Pages.

(Continued)

*Primary Examiner* — Catherine Voorhees
(74) *Attorney, Agent, or Firm* — Brooks Kushman P.C.

(57) ABSTRACT

A high frequency surgery generator having an output circuit and a power oscillator for generating an HF output voltage. The power oscillator is designed to excite the output circuit at a first excitation frequency, which corresponds to a resonant frequency of the output circuit, in a first operating mode and to excite the output circuit at a second excitation frequency which differs from the first excitation frequency, which does not correspond to the resonant frequency of the output circuit, in a second operating mode.

4 Claims, 2 Drawing Sheets

(56) References Cited

U.S. PATENT DOCUMENTS

| | | | |
|---|---|---|---|
| 6,416,509 B1 * | 7/2002 | Goble et al. | 606/37 |
| 7,244,255 B2 | 7/2007 | Daners et al. | |
| 7,648,499 B2 * | 1/2010 | Orszulak et al. | 606/34 |
| 2004/0193148 A1 | 9/2004 | Wham et al. | |

FOREIGN PATENT DOCUMENTS

| | | |
|---|---|---|
| DE | 69715452 T2 | 2/2003 |
| DE | 10218895 A1 | 11/2003 |
| EP | 1776929 A1 | 4/2007 |
| JP | 2001506895 | 5/2001 |
| JP | 2002360712 | 12/2002 |
| WO | 9827880 A1 | 7/1998 |

OTHER PUBLICATIONS

Japanese Office Action for JP 2012-541379, Dated Mar. 11, 2014, English Translation attached to original, All together 7 Pages.
Chinese Office Action and Search Report for Chinse application No. 201080053783.X, Dated Jun. 4, 2014, 7 Pages.

* cited by examiner

HIGH FREQUENCY SURGERY GENERATOR

CROSS-REFERENCE TO RELATED APPLICATION

This application is the U.S. national phase of PCT Application No. PCT/EP2010/066726 filed on Nov. 3, 2010, now published WO 2011/067061, which claims priority to DE Patent Application No. 102009044720.2 filed on Dec. 1, 2009 and DE Patent Application No. 102010000184.8 filed on Jan. 25, 2010, the disclosures of which are incorporated in their entirety by reference herein.

FIELD OF THE INVENTION

The invention relates to an electrosurgical generator for producing an RF output voltage.

BACKGROUND

These days, electrosurgery is used in many medical fields. In the process, a relatively high voltage, which is applied to a monopolar or bipolar electrode, is used to damage or cut biological tissue in a targeted manner. In order to produce these voltages, use is usually made of an electrosurgical generator (RF surgical generator).

Different types of modulation are used for cutting and/or coagulating the biological tissue. To this end, e.g. bursts must have a quick beginning and end.

EP 1 776 929 A1 describes an electrosurgical generator in which the output voltage of the RF surgical generator can quickly be reduced. In the process, if a threshold is exceeded, the output voltage of the RF surgical generator is quickly reduced by virtue of converting the energy from the power supply unit into heat by connecting an additional load component. A disadvantage of this is that the generated heat needs to be dissipated and that the RF surgical generator is technically complex and has poor cutting properties.

DE 102 18 895 A1 describes a further electrosurgical generator, wherein the output voltage of the electrosurgical generator can quickly be reduced. Here, the output voltage of the power supply unit is reduced by virtue of feeding the output capacitor energy back to the DC voltage supply. As a result, the energy stores on the output side of the DC voltage supply and in the power oscillator are quickly discharged. As a result of this, the output voltage of the electrosurgical generator is quickly reduced. A disadvantage of this is that the electrosurgical generator offers poor cutting properties and the circuit is complicated and technically complex.

US 2004/0193148 A1 describes an electrosurgical generator in which surges in the output voltage of the RF surgical generator can quickly be regulated down. In this case, the resonant frequency of the oscillator is modified by the addition of further components as soon as the output voltage of the RF surgical generator lies above a limit voltage. As a result, the unchanging excitation frequency no longer corresponds to the resonant frequency of the oscillator, as a result of which the output voltage of the RF surgical generator is reduced below the limit voltage, i.e. to the level of a normal output voltage, and sparking is prevented. It is disadvantageous in this case that the circuit is technically complex and sparking, which is advantageous for cutting, is prevented and hence the RF surgical generator offers poor cutting properties.

SUMMARY

The invention is based on the object of highlighting an RF surgical generator.

This object is achieved by an RF surgical generator. An essential point of the invention consists of the fact that the RF surgical generator comprises two operating modes: in the first operating mode, an output circuit is excited by an RF power oscillator with a resonant frequency of the output circuit. In a second operating mode, the output circuit is excited by the RF power oscillator with another frequency that does not correspond to the resonant frequency thereof. The output voltage of the RF surgical generator is quickly and abruptly reduced in the case of a transition from the first operating mode to the second operating mode.

As a result of this, output voltages with harmonics are produced and this results in improved cutting properties of the RF surgical generator. Moreover, the RF surgical generator is simple from a technical point of view and cost effective.

The RF power oscillator can comprise switching elements, more particularly transistors, for controlling a sign of an excitation voltage, by means of which switching elements the RF power oscillator excites the output circuit in a feedback operation in the first operating mode depending on a sign of an excitation current of the RF power oscillator, and for setting the second excitation frequency in a second, forced operating mode. As a result of this, in the first operating mode, the output circuit can be driven in a technically simple manner with as little energy loss as possible using a resonant frequency. The fact that the frequency of the excitation voltage in the second operating mode can be set in a technically simple manner is also advantageous in this case.

In one embodiment, the electrosurgical generator comprises a controllable operating-mode switching device for switching from the first operating mode to the second operating mode for producing an output voltage with harmonics. An advantage of this is that an output voltage with harmonics that is very advantageous for cutting the tissue can be set in a targeted manner.

The RF surgical generator can comprise an adjustable frequency control instrument for measuring a sign of the excitation current and for opening and/or closing the switching elements for controlling a sign of the excitation voltage in the first operating mode and for setting the second excitation frequency in the second operating mode. As a result of this, the sign of the excitation current can be captured in a technically simple manner and the sign of the excitation voltage can accordingly be set in the first operating mode. The fact that the excitation frequency can be set in a targeted manner in the second operating mode is also advantageous in this case.

In terms of the method, the invention is achieved by virtue of the fact that the RF power oscillator excites the output circuit in a first operating mode with a first excitation frequency, which corresponds to a resonant frequency of the output circuit, for producing the RF output voltage and that the RF power oscillator excites the output circuit in a second operating mode with a second excitation frequency that differs from the first excitation frequency and does not correspond to the resonant frequency of the output circuit for the accelerated reduction of the RF output voltage.

BRIEF DESCRIPTION OF THE DRAWINGS

Preferred embodiments of the invention emerge from the dependent claims. In the following text, the invention will be explained in more detail on the basis of drawings of exemplary embodiments. In this case:

In the following description, the same reference signs are used for equivalent and functionally equivalent parts.

DETAILED DESCRIPTION

Figure 1:
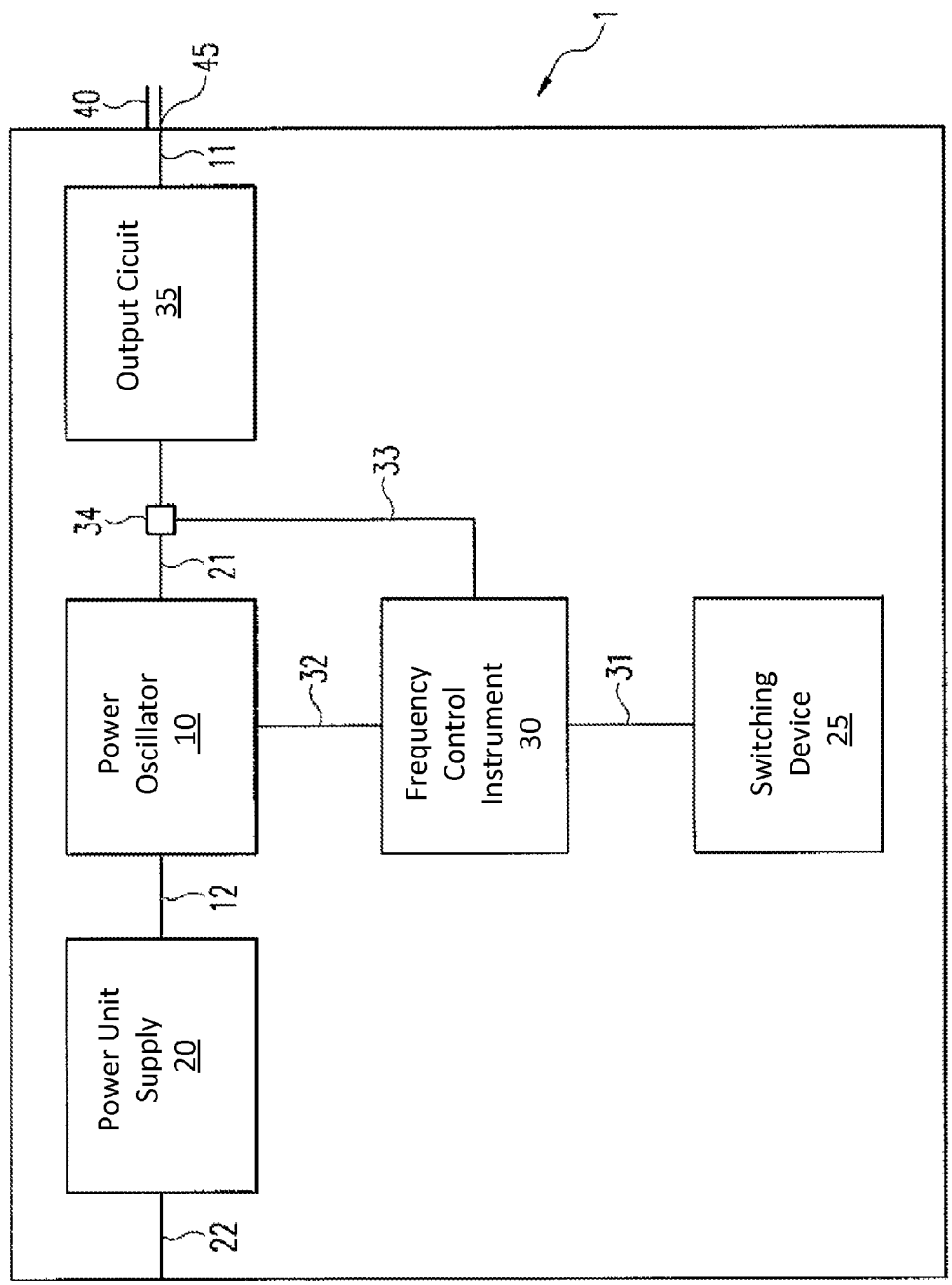
FIG. 1 shows a schematic view of an RF surgical generator.

FIG. 1 shows a schematic view of an RF surgical generator 1. The RF surgical generator 1 comprises a power supply unit 20, which is connected to a current and voltage supply (not illustrated) via connection lines and which supplies a power oscillator 10 with electrical energy via a connection line 12. The power oscillator 10 is connected to an output circuit 35 via a connection line 21. The power oscillator 10 drives the output circuit 35 with an excitation frequency. The output circuit 35 is connected to one of the outputs 45 of the RF surgical generator 1 via a connection line 11. A monopolar or bipolar electrode 40, to which an output voltage of the RF surgical generator 1 is applied, can be connected to the outputs 45.

In the first operating mode, the output circuit 35 is excited by the power oscillator 10 with a first excitation frequency which corresponds to a resonant frequency or the resonant frequency of the output circuit 35. At a resonant frequency of the output circuit 35, there is a maximum of the amplitude transfer function $|A(f)|=|u_{out}/u_{in}|$ (where $u_{in}$ is the voltage which is applies at the output of the power oscillator and $u_{out}$ is the voltage applied at the output of the output circuit, i.e. at the output of the RF surgical generator 1). The maximum power is transmitted at the resonant frequency. In general, this is also the work point with the highest energetic efficiency.

This excitation in the first operating mode of the output circuit 35 with an excitation frequency that corresponds to the resonant frequency of the latter or one of the resonant frequencies of the latter is brought about as follows: the frequency control instrument 30 measures the sign of the output current of the power oscillator 10, i.e. the phase in which the output current currently is, with the aid of an ammeter via a connection line 33. Depending on this, the frequency control instrument 30 accordingly sets the sign of the output voltage of the power oscillator 10 via a connection line 32 such that the output voltage of the power oscillator 10 is in phase with the output current of the power oscillator 10.

In the second operating mode, the output current 35 is excited by the power oscillator 10 with a second excitation frequency, which does not correspond to the first excitation frequency, by virtue of, independently of the phase of the output current of the power oscillator 10, setting the output voltage of the power oscillator 10 to a frequency which corresponds to the second excitation frequency. The second excitation frequency is set by the frequency control instrument 30. The second excitation frequency is not in the vicinity of the resonant frequency of the output circuit 35, i.e. the second excitation frequency differs not only insubstantially from the resonant frequency, because the amplitude transfer function is near its maximum at a frequency close to the resonant frequency.

In the case of this second excitation frequency, the amplitude transfer function is not at its maximum and far from it. As a result, the output voltage and output power of the output circuit 35 reduces and hence the output voltage of the RF surgical generator 1 is quickly reduced or lowered. Moreover, the generator internal resistance of the RF surgical generator 1 abruptly increases as a result of this.

When operating the RF surgical generator 1 in the second operating mode, the output circuit 35 supplies output current forms and output voltage forms with substantial harmonics. This promotes sparking at the electrode 40. Sparking at the electrode 40 is particularly desirable if biological tissue is intended to be cut using the electrode 40. The second operating mode makes it possible to produce output voltages or output voltage forms with harmonics in the case of an otherwise low-distortion surgical generator.

An operating-mode switching device 25 is connected to the frequency control instrument 30 via a connection line 31. As a result of this it is possible to switch between a first operating mode and a second operating mode or from the first operating mode to the second operating mode. This can be used in a targeted manner to set the second operating mode, in which tissue can be cut.

Moreover, an emergency button can for example be connected to the operation switching device 25 such that, in the case of an emergency, the output voltage of the RF surgical generator 1, i.e. the voltage at the electrode 40, can be rapidly reduced if the surgeon or another person actuates the emergency button.

The RF surgical generator 1 can comprise an indicator, for example in the form of indicator lamps, which shows which operating mode the RF surgery generator 1 is currently in.

In the second operating mode, the power oscillator 10 always drives the output circuit 35 with the same low-resistance source impedance.

This ensures that the output frequency of the output circuit 35 always corresponds to the set frequency of the power oscillator 10.

The cutting properties of the RF surgical generator are also improved by the RF surgical generator 1 highlighted here in the case of surroundings of the connected electrode 40 consisting of a conductive liquid, such as e.g. physiological saline, as a result of the output voltage with harmonics in the second operating mode.

Figure 2:
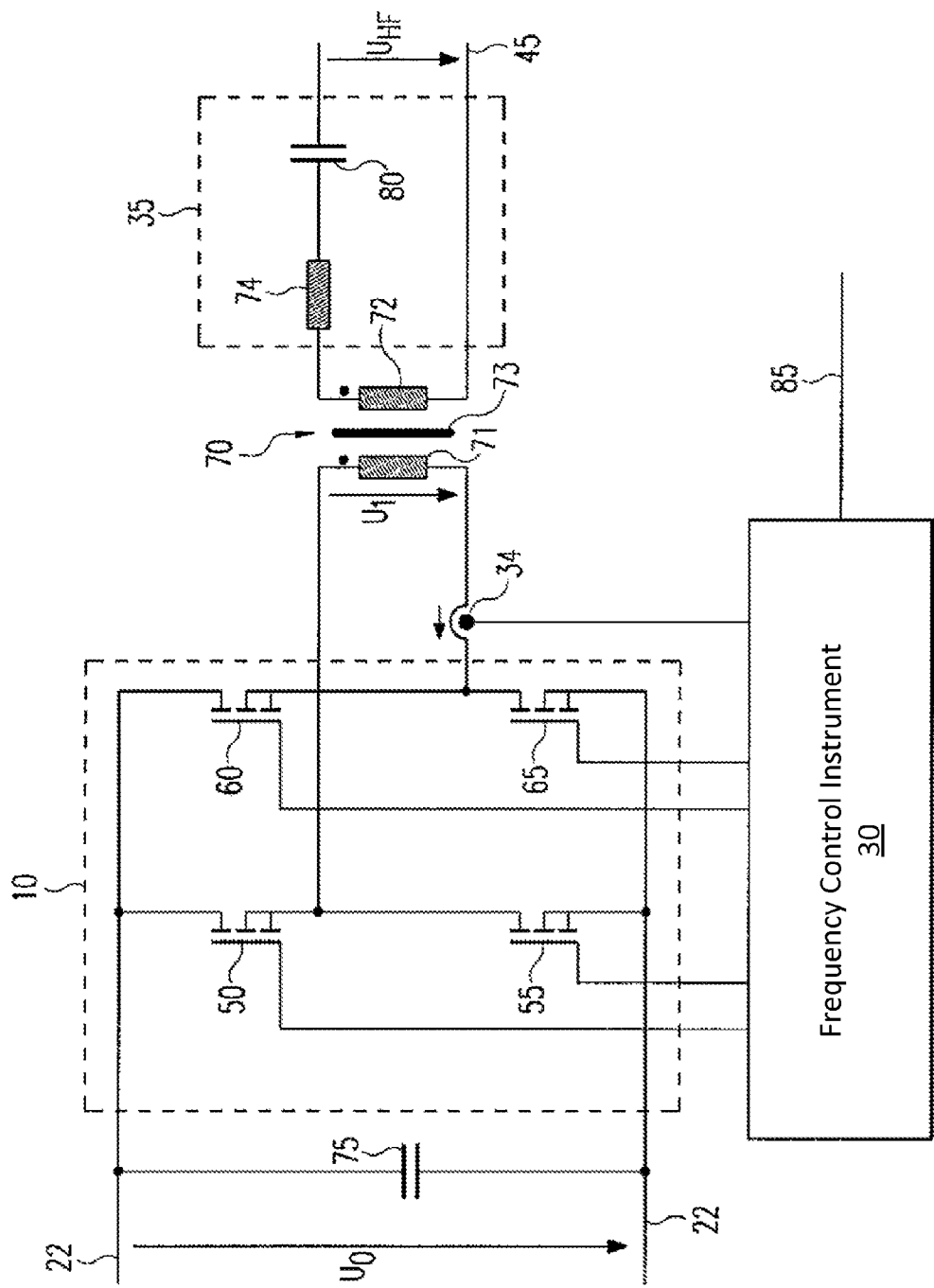
FIG. 2 shows a schematic view of a circuit design in a power supply unit and in a power oscillator of an RF surgical generator.

FIG. 2 shows a circuit design of a second embodiment of an RF surgical generator 1. The power oscillator 10 is connected to a power supply unit (not shown) via connection lines 22. The power supply unit supplies a voltage U0, which is applied across a first capacitor 75. The power oscillator 10 is connected to the output circuit 35 via a transformer 70. There is galvanic isolation between the electrical circuits of the RF power oscillator 10 and the output circuit 35 as a result of the transformer 70. The transformer 70 comprises a first inductor 71 and a second inductor 72, which are coupled across a magnetic core 73. The power oscillator 10 comprises four transistors 50, 55, 60, 65. A voltage U1 is applied to the transformer on the side of the power oscillator 10. A frequency control instrument 30 measures the sign of a current I1 at the output of the power oscillator 10 with the aid of an ammeter 34.

The inputs of the first transistor 50 and the third transistor 60 are connected to the power supply unit via one of the connection lines 22. The output of the first transistor 50 is connected to a connector of the first inductor 71 and to the input of the second transistor 55. The output of the third transistor 60 is connected to an output of the ammeter 34 and to the input of the fourth transistor 65. The outputs of the second transistor 55 and the fourth transistor 65 are connected to the power supply unit via one of the other connection lines 22.

The frequency control instrument 30 is connected to a frequency generator (not shown here) via a connection line

85. The frequency control instrument 30 is respectively connected to the control connector of the first 50, second 55, third 60 and fourth transistor 65.

If the value of I1, measured by the ammeter 34, is greater than zero, the frequency control instrument 30 turns the first transistor 50 and the fourth transistor 65 on. If the frequency control instrument 30 determines that I1 is less than or equal to zero, the frequency control instrument 30 turns the third transistor 60 and the second transistor 55 on. The other two transistors are respectively turned off.

The output circuit 35 furthermore comprises a third inductor 74 and a second capacitor 80. These are connected to one of the outputs 45 of the RF surgical generator 1. The radiofrequency voltage UHF is applied to the outputs 45. As a result of control by the frequency control instrument 30, the output voltage U1 and the output current I1 of the RF power oscillator are in phase and the amplitude transfer function is at its maximum or in the vicinity thereof.

In the second operating mode, the output circuit 35 is excited by a resonant-distant excitation frequency. A resonant-distant frequency should be understood to mean a frequency which does not equal the resonant frequency of the output circuit 35 and which also does not only deviate insubstantially from the resonant frequency. In the second operating mode, the first transistor 50 and the fourth transistor 65 and also the second transistor 55 and the third transistor 60 are alternately turned on with respectively half the period duration of the desired second excitation frequency, independently of the sign of the excitation current I1. The respective other two transistors are turned off. This second excitation frequency is transmitted to the frequency control instrument 30 by means of the frequency generator. The second excitation frequency transmitted by the frequency generator can be set. The amplitude transfer function is (further) away from its maximum in the second operating mode.

At this point, reference is made to the fact that all parts described above, more particularly the details illustrated in the drawings, are claimed as essential to the invention, either when considered on their own or in any combination. A person skilled in the art is aware of modifications of this.

LIST OF REFERENCE SIGNS

1 RF surgical generator
10 RF power oscillator
11 Output circuit—output connection line
12 Power supply unit—RF power oscillator connection line
20 Power supply unit
21 RF power oscillator—output circuit connection line
22 Power supply unit—current source connection line
25 Operating-mode switching device
30 Frequency control instrument
31 Frequency control instrument—operating-mode switching device connection line
32 Frequency control instrument—RF power oscillator connection line
33 Frequency control instrument—ammeter connection line
34 Ammeter
35 Output circuit
40 Electrode
45 Outputs of the RF surgical generator
50 First transistor
55 Second transistor
60 Third transistor
65 Fourth transistor
70 Transformer
71 First inductor
72 Second inductor
73 Magnetic core
74 Third inductor
75 First capacitor
80 Second capacitor
85 Frequency generator—frequency control connection line

The invention claimed is:

1. An electrosurgical generator for generating an RF output voltage, comprising: an output circuit and an RF power oscillator for exciting the output circuit with a first excitation frequency, which corresponds to a resonant frequency of the output circuit, in a first operating mode,
   wherein the RF power oscillator is configured for exciting the output circuit with a second excitation frequency that differs from the first excitation frequency and does not correspond to the resonant frequency of the output circuit in a second operating mode by setting the output voltage of the RF power oscillator to the second excitation frequency independently of the phase of the output current of the power oscillator, and
   wherein the RF power oscillator comprises switching elements (i) for controlling a direction of an excitation voltage, wherein the RF power oscillator excites the output circuit in a feedback operation in the first operating mode depending on a direction of an excitation current of the RF power oscillator by said switching elements so that the RF power oscillator drives the output circuit, and (ii) for setting the second excitation frequency in the second operating mode.

2. The electrosurgical generator as claimed in claim 1, wherein the generator comprises a controllable operating-mode switching device for switching from the first operating mode to the second operating mode wherein the second operating mode produces an output voltage with harmonics.

3. The electrosurgical generator as claimed in claim 2, wherein the generator comprises an adjustable frequency control instrument
   for measuring the direction of the excitation current and for opening and/or closing the switching elements for setting the direction of the excitation voltage in the first operating mode and
   for setting the second excitation frequency in the second operating mode.

4. A method for operating an electrosurgical generator with an RF power oscillator and an output circuit, comprising the following steps:
   exciting the output circuit by the RF power oscillator in a first operating mode with a first excitation frequency, which corresponds to a resonant frequency of the output circuit, for producing the RF output voltage,
   exciting the output circuit by the RF power oscillator in a second operating mode with a second excitation frequency that differs from the first excitation frequency and does not correspond to the resonant frequency of the output circuit for the accelerated reduction of the RF output voltage by setting the output voltage of the power oscillator to the second excitation frequency independently of the phase of the output current of the power oscillator,
   measuring a direction of an excitation current in the RF power oscillator, and
   controlling the state of switching elements for controlling the direction of the excitation voltage in the RF power oscillator depending on a direction of the excitation current in the RF power oscillator in a feedback operation in the first operating mode so that the RF power oscillator drives the output circuit and for setting the second excitation frequency in a second, forced operating mode.

* * * * *

UNITED STATES PATENT AND TRADEMARK OFFICE
CERTIFICATE OF CORRECTION

PATENT NO. : 9,192,423 B2  
APPLICATION NO. : 13/512840  
DATED : November 24, 2015  
INVENTOR(S) : Heiko Schall et al.

Page 1 of 1

It is certified that error appears in the above-identified patent and that said Letters Patent is hereby corrected as shown below:

On the title page item (30), under the heading, Foreign Application Priority Data, and after "Jan. 25, 2010 (DE) . . . . . . . . . . . . . . . 10 2010 000 184" insert:

--Dec. 1, 2009 (DE) . . . . . . . . . . . . . . . 10 2009 044 720--.

Signed and Sealed this  
Twenty-sixth Day of April, 2016

Michelle K. Lee  
*Director of the United States Patent and Trademark Office*